United States Patent
Basler et al.

(10) Patent No.: US 6,454,629 B1
(45) Date of Patent: Sep. 24, 2002

(54) METHOD FOR THE PRODUCTION OF MEDICAL FITTINGS, IN PARTICULAR DENTAL FITTINGS

(75) Inventors: Franz Basler, Laudenbach; Volker Wedler, Heddesheim; Bernd Rothenberger, Gernsbach, all of (DE)

(73) Assignee: Sirona Dental Systems GmbH, Bensheim (DE)

( * ) Notice: Subject to any disclaimer, the term of this patent is extended or adjusted under 35 U.S.C. 154(b) by 146 days.

(21) Appl. No.: 09/610,358

(22) Filed: Jul. 5, 2000

(30) Foreign Application Priority Data

Jul. 5, 1999 (DE) .......................................... 199 30 859

(51) Int. Cl.⁷ .......................... B24B 49/00; B24B 51/00
(52) U.S. Cl. ............................... 451/5; 451/27; 451/51; 451/9; 451/10
(58) Field of Search ................................. 433/166, 223; 451/5, 8, 9, 10, 11, 41, 27, 51, 52; 408/3; 409/2, 79, 289

(56) References Cited

U.S. PATENT DOCUMENTS

| 4,411,626 A | * | 10/1983 | Becker et al. | 433/223 |
| 5,310,342 A | * | 5/1994 | Bernstein | 433/166 |
| 5,490,810 A | * | 2/1996 | Hahn et al. | 433/223 |
| 5,743,686 A | * | 4/1998 | Montgomery | 433/223 |

* cited by examiner

*Primary Examiner*—Timothy V. Eley
(74) *Attorney, Agent, or Firm*—Dykema Gossett PLLC

(57) ABSTRACT

A method for the production of medical fittings, in particular dental fittings, is proposed. A workpiece (1), from which the fitting is produced, has material removed from it by machining with a tool (7). The tool (7) and the workpiece (1) execute a relative movement with respect to each other along a fixed trajectory. The instantaneous loading of the tool is used to control the speed of this relative movement. In order to avoid the load peaks which occur here, and to ensure a more uniform control, it is proposed that the expected loading of the tool along the trajectory is also calculated and is used to control the speed.

13 Claims, 2 Drawing Sheets

METHOD FOR THE PRODUCTION OF MEDICAL FITTINGS, IN PARTICULAR DENTAL FITTINGS

BACKGROUND OF THE INVENTION

The invention relates to a method for the production of medical fittings, in particular dental fittings, in which a workpiece, from which the fitting is produced, has material removed from it by machining with a tool.

A method of this type is known from EP-A-0,182,098, for example. A workpiece made of dental ceramic material is arranged on a holder which advances with rotation as the machining is carried out. In doing so, the workpiece is alternately machined by a cutting wheel or a finger-shaped grinder rod which are arranged on a tool carrier. The height position of the tool carrier is controlled by a program in such a way that the shaping by material removal is effected along the intended contour of the fitting. The contour to be formed has been obtained in advance from a visual scan of the pretreated tooth into which the dental fitting is to be implanted.

A method for the production of dental prosthetic fittings is also known from EP-A-0,455,853. Here, the machining is effected simultaneously by two tools mounted on different tool heads.

A problem during machining of the workpiece is that the removal capacity of the tools is in most cases not constant along the intended contour of the fitting. A great deal of material is removed at some points of the contour, in particular if a fitting with steep flanks or sizeable depressions is to be produced. At other 5 points, by contrast, the amount of material removed can be very slight, e.g. if a flat, smooth surface is to be obtained.

Too high a removal capacity can lead to overheating the tool or even to its destruction. It is therefore highly important to ensure that a maximum loading of the tools is not exceeded throughout the machining of the workpiece.

For this purpose, it has been proposed, with a constant frequency of rotation of the rotating tool, to constantly monitor the power consumption of the rotary drive mechanism. This power consumption then represent a measure for the instantaneous loading of the tool. If the power consumption exceeds a defined maximum value, the speed of advance between workpiece and tool is reduced until the power consumption once again falls below the maximum value.

It is true that satisfactory control can in many cases be achieved using such a method. However, this control is often not sufficient to reliably avoid power peaks, which can lead to greatly increased wear of the tool. Such power peaks can occur particularly upon rapid change over between a low removal capacity and a high removal capacity. This is often the case, for example, when producing sharp-edged structures with steep flanks, as are often found in tooth crowns.

SUMMARY OF THE INVENTION

The object of the invention is therefore to provide a method for the production of medical fittings, in which method load peaks of the tools can be effectively avoided and the fitting can be finished in the shortest possible time.

This object is achieved by means of a method for the production of medical fittings, in particular dental fittings, in which a workpiece, from which the fitting is produced, has material removed from it by machining with a tool, the tool and the workpiece executing a relative movement along a trajectory, and the actual loading of the tool being used to control the speed of the relative movement. According to the invention, the expected loading of the tool along the trajectory is calculated and is used to control the speed.

As the expected removal capacity of the tool is already calculated in advance, even very rapid load changes can be detected in good time and taken into account in controlling the movement between workpiece and tool. In this way, power peaks are effectively ruled out from the outset. Whereas, for example, a low speed between tool and workpiece is chosen in advance for those parts of the trajectory in which a high removal capacity is to be expected, the movement in regions with only slight removal can be very fast. This leads to a considerable saving in time during production of the fittings. Moreover, the forces between tool and workpiece are reduced.

This method can be used to particular advantage when the tool is essentially cylindrically symmetrical and rotates about its axis of symmetry by means of a rotary drive mechanism. The tool is advantageously an essentially cylindrical grinder rod with a circumferential surface and an end surface.

There are two possibilities in particular for determining the instantaneous loading of the tool. According to the first possibility, the measure for the actual loading of the tool is the frequency of rotation of the tool determined at an essentially constant power consumption of the rotary drive mechanism. According to the second possibility, the measure for the actual loading of the tool is the power consumption of the rotary drive mechanism determined at a predetermined frequency of rotation.

The types of relative movement between the tool and the workpiece are often defined by the device with which the fitting is produced. The method according to the invention can be used to particular advantage if the relative movement between the tool and the workpiece includes the following types of movement:

a) linear feed between the tool and the workpiece along a feed direction which is essentially perpendicular to the axis of symmetry of the tool;

b) change of depth of the tool in the workpiece essentially along the axis of symmetry of the tool; and c) one-dimensional sideways movement between the tool and the workpiece along a predetermined path in a plane which is essentially perpendicular to the axis of symmetry of the tool and is different than the direction of the linear feed.

The one-dimensional sideways movement preferably consists of a swiveling of the tool about an axis which is essentially parallel to the axis of symmetry of the tool. However, another possibility is a transverse movement of the tool along a direction which is essentially perpendicular both to the axis of symmetry of the tool and also to the direction of the linear feed.

In order to be able to form complicated structures from the workpiece, it can be expedient if the relative movement between the tool and the workpiece moreover includes a pivoting of the workpiece about an axis which is essentially parallel to the direction of the linear feed.

The desired contour is advantageously obtained from the workpiece by the linear feed taking place in steps in the same direction throughout machining. The feed in this case preferably takes place in steps which are small compared to the mean diameter of the tool. The trajectory is divided into sections between which no linear feed takes place. The expected loading for each section is then calculated by comparison of the trajectory along this section and the trajectory of the respective previous section. Each movement section can be made up of said movement types b) and c), that is to say a change of depth of the tool and a one-dimensional sideways movement. The expected removal capacity can be calculated at least one previously chosen point of the movement section.

If the tool is a cylindrical grinder rod, it is advantageous to calculate the expected loading in the following manner: In order to determine a measure for the expected loading upon a change of depth of the grinder rod in the workpiece, that part of the end face is approximately determined from which material is removed. The speed of the change of depth of the tool in the workpiece is then limited to a maximum speed which is determined by reference to a table in which, for several values of that portion of the end face from which material is removed, the associated maximum speed is stored.

The one-dimensional sideways movement is controlled in a similar way. In order to determine a measure for the expected loading upon the one-dimensional sideways movement, the height of that part of the circumferential surface of the grinder rod from which material is removed is calculated. The speed of the one-dimensional sideways movement is then limited to a maximum speed which is determined by reference to a table in which, for a number of values of the height of that portion of the circumferential surface from which material is removed, the associated maximum speed is stored.

BRIEF DESCRIPTION OF THE DRAWINGS

Advantageous embodiments of the method according to the invention are explained with reference to the drawing, in which.

DETAILED DESCRIPTION OF THE INVENTION

Figure 1:
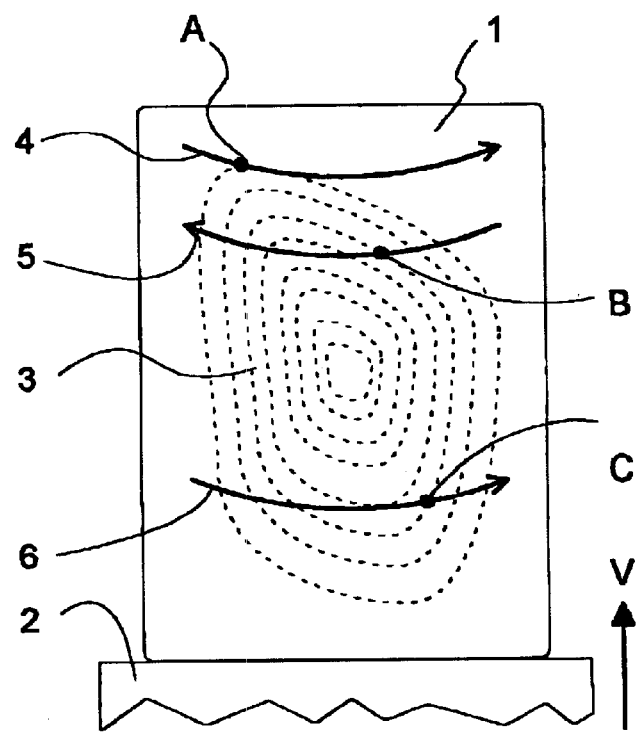
FIG. 1 is a diagrammatic sketch showing the machining of the workpiece.

In FIG. 1, a workpiece 1 is mounted on a holder 2. The latter is clamped in a workpiece spindle (not shown) and can be moved in the axial direction along the direction of feed V by means of the workpiece spindle. Arranged above the plane of the drawing there is a cylinder grinder (not shown) which is mounted in a tool spindle and can be set in rotation by means of a rotary drive mechanism. The cylinder grinder rotates about an axis which is perpendicular to the plane of the drawing and thus also perpendicular to the direction of feed V.

By means of a suitable drive device, the cylinder grinder in the tool spindle can be moved along the axis of rotation of the tool, that is to say perpendicular to the plane of the drawing, toward the tool and away from it. This corresponds to a change of depth of the cylinder grinder in the workpiece along the axis of symmetry of the grinder. In addition, the tool spindle can be swiveled about an axis (not shown) in the plane of the drawing. In doing so, the cylinder grinder describes a circular arc trajectory relative to the workpiece. A number of such trajectories, dependent on the instantaneous feed of the workpiece along V, are shown in FIG. 1 by 4, 5 and 6.

To illustrate the pattern of movement upon machining of the workpiece, it has been assumed that, in the course of machining, a contour is to be produced in the workpiece 1 as indicated by the contour lines 3. This contour accordingly consists of an irregularly shaped depression in the workpiece 1 directed into the plane of the drawing. Such a contour can, for example, be the masticatory surface of a tooth crown which is to be made from the workpiece.

At the start of machining, the workpiece spindle, with the holder 2 and the workpiece 1 secured thereon, is situated in its starting position relative to the direction of feed V. The cylinder grinder is thus situated at the upper end of the workpiece 1 relative to the direction of feed V. After a null compensation of the tools, as is described in EP-A-0,455,853, for example, the actual machining process begins. For this purpose, the grinder rod is brought to position A by suitable advance of the workpiece in the direction V and by suitable swiveling of the tool spindle. The rotating grinder rod now begins to machine the workpiece by being moved to the workpiece along its axis of rotation until its end face touches the workpiece and begins removing material.

As soon as the grinder rod has penetrated by the desired amount into the workpiece, the tool spindle is swiveled along the direction 4, a change of depth of the grinder rod in the workpiece being effected continuously or in steps. In this way, the first trajectory section of the contour to be formed is generated.

As soon as the machining along this section has been completed, the workpiece 1 is moved a small distance along the direction of feed V. The extent of the feed step depends in particular on the desired precision on production of the contour. However, in any event it is very much smaller than the diameter of the grinder rod.

After this feed step has been effected, the tool spindle is then swiveled back along a trajectory parallel to the direction 4, the depth of the grinder rod in the workpiece changing continuously, and thus a second section of the contour to be generated is formed. This sequence of feed steps and subsequent working of the contour along a trajectory section by swiveling of the tool spindle and changing the depth of the tool is continued until the entire contour has been formed. The feed always takes place in the same direction along the direction of feed V.

Figure 2:
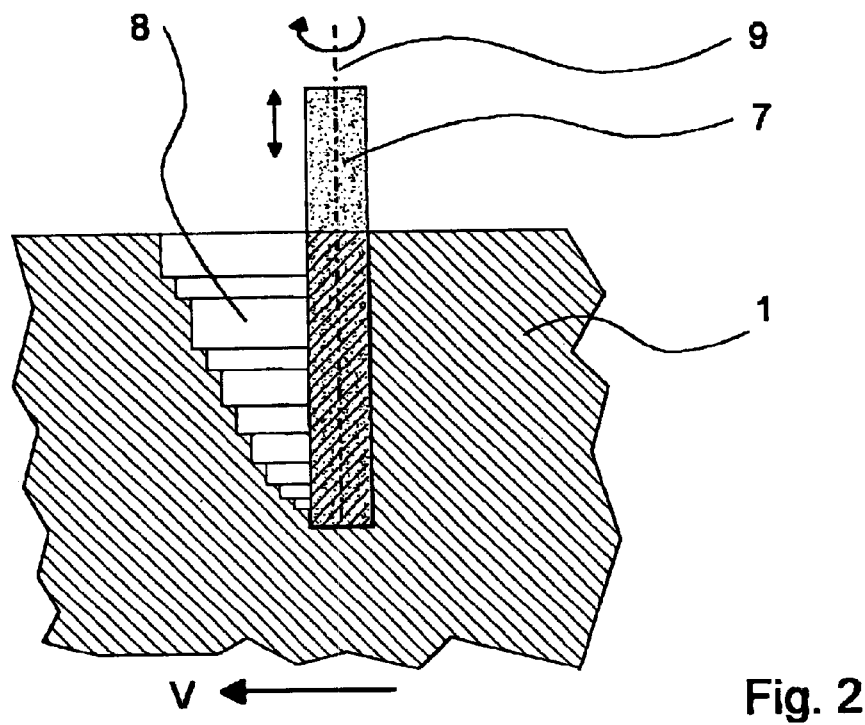
FIG. 2 shows the position of the grinder rod in the workpiece in a first machining phase.
Figure 3:
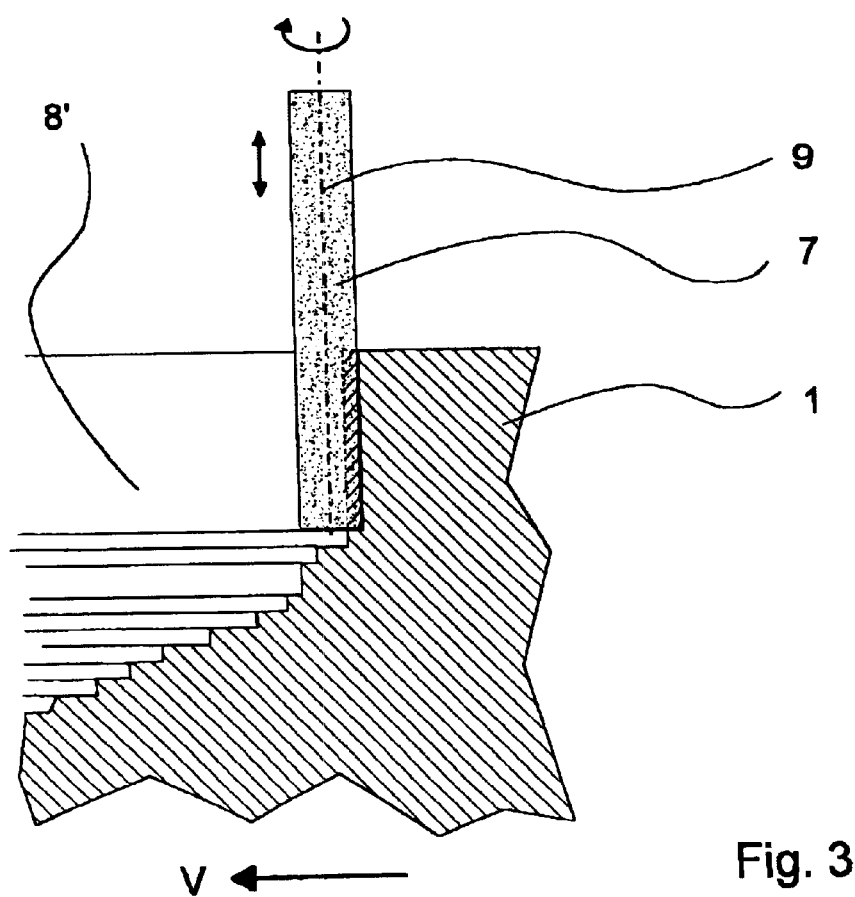
FIG. 3 shows the position of the grinder rod in the workpiece in a second machining phase.

FIGS. 2 and 3 illustrate the removal of the workpiece material in different phases during machining of the workpiece 1. The representation of FIGS. 2 and 3 is in section from the side, the direction of viewing relative to FIG. 1 being from the left within the plane of the drawing. The situation in FIG. 2 corresponds roughly to the state at point B, while the situation in FIG. 3 corresponds roughly to the state at point C. Both FIG. 2 and FIG. 3 are thus to be considered as highly diagrammatic representations, and in particular not true to scale.

In FIG. 2, the grinder rod 7, after a number of feed steps, has reached the illustrated position in the workpiece 1. In so doing, it has formed the area 8 of the desired contour out of the workpiece 1. After a further feed step of the workpiece 1 in the direction V, the grinder rod 7 then forms a further section of the contour from the workpiece 1. For this purpose, it is swiveled with the tool spindle, which corresponds to a movement into or away from the plane of the drawing, and its depth in the workpiece is changed, which corresponds to an upward or downward movement of the grinder rod along the axis of rotation 9.

The same applies analogously to FIG. 3. A larger part 8' of the desired contour has now been formed in the workpiece 1. Here too, after each feed step in the direction V, the tool moves into or away from the plane of the paper and upward or downward along the axis of rotation 9.

During the machining of the workpiece 1, it is possible to differentiate between various types of load or load cases for the grinder rod 7. The first load case is the so-called end-face load case. This occurs when the grinder rod 7 is moved along its axis of rotation into the workpiece 1. Material is in this case removed only from the end face of the grinder rod. Various situations are to be differentiated here. In the first situation, the entire end face of the grinder rod takes part in removing material. This is the case, for example, when, in FIG. 2, the grinder rod 7 is moved downward along its axis of rotation. This can be referred to as a complete end-face load case. In the other situation, only part of the end face takes part in removing material. This is the case, for example, when the grinder rod 7 in FIG. 3 is moved downward along its direction of rotation. Here, in FIG. 3, material is removed only at the lower right end of the grinder rod.

A similar distinction can also be made for the swiveling of the grinder rod into and away from the paper plane. If, for example, in FIG. 2, the grinder rod is swiveled far enough into the paper plane, material removal takes place on a relatively large part of the circumferential surface. This part lies on the reverse side of the grinder rod in FIG. 2 and is indicated by the separate hatching. There is therefore a high circumferential load. In FIG. 3, by contrast, material is removed only with a relatively small portion of the circumferential surface of the grinder rod 7, again indicated by the hatching.

It is therefore evident that in the course of machining of the workpiece very different loads on the tool (grinder rod 7) can occur.

In order to avoid overloading of the tool occurring here, a number of variants are conceivable. The first and simplest variant consists in limiting the speed of the relative movement between tool and workpiece to a low maximum value throughout the period of machining. If the chosen speed is sufficiently low, this means that no overloading of the tool can occur, even in the most unfavorable load case. Although it is possible to effectively avoid overloading of the tool by means of such a procedure, the time for machining of the workpiece increases unacceptably.

A second variant, which has hitherto been employed in the prior art, consists in continuously determining the loading of the tool and controlling the relative movement between tool and workpiece on the basis of the determined loading. To do so, the frequency of rotation of the tool for example is controlled in such a way that this remains essentially constant; the power consumption of the tool drive mechanism is then determined, for example by measuring the current of an electrical tool drive mechanism. This power consumption is a direct measure for the instantaneous loading of the tool. The relative speed between tool and workpiece is then controlled in such a way that, at a high load, the relative speed between tool and workpiece is lowered, and vice versa. With ideal, instantaneous functioning of such a control, the workpiece could be machined with a constant removal capacity and a constant loading of the tool.

In particular, this control of the relative speed is by itself inadequate in the event of rapid load changes. According to the present invention, it is supplemented by predetermining the expected removal capacity or tool loading. In this way, the movement between tool and workpiece can be chosen in advance to be very slow in those areas where a high removal capacity is expected, and, conversely, in those areas where only a low removal capacity is expected, a higher relative speed between tool and workpiece can be chosen.

Figure 4:
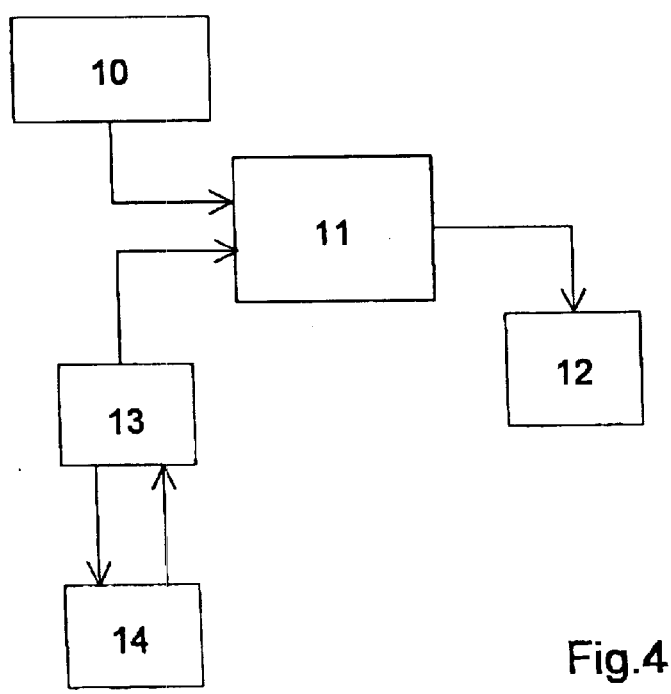
FIG. 4 shows a diagrammatic plan of the control sequence.

The sequence of the method according to the invention is illustrated diagrammatically in FIG. 4. The geometric data of the fitting which is to be produced are stored in a computing and storage unit 10. In the case of production of a dental prosthetic fitting, these data can be obtained, for example in a manner known per se, from an optical 3D image of an area of the oral cavity. From these geometric data, the computing and storage unit 10 calculates, on the one hand, the trajectory on which the machining tool and the workpiece move relative to each other, and, on the other hand, the expected removal capacity of the tool at a number of points on this trajectory. Finally, the computing and control unit 10 calculates control signals from these which it forwards to a control unit 11. The control unit 11 controls various electromotor, hydraulic or pneumatic drive mechanisms which are provided for executing a relative movement between tool and workpiece. In FIG. 4, these drive mechanisms are shown diagrammatically, combined into one drive unit 12. In addition to the control signals from the computing and control device 10, the control device 11 also obtains signals from a drive mechanism control 13 with the aid of which the electromotor rotational drive mechanism 14 of the machining tool is controlled. The control is effected in such a way that the frequency of rotation of the machining tool remains essentially constant. The control unit 11 is then supplied with signals containing information on the power consumption of the rotational drive mechanism 14. From the signals of the computing and control unit 10, on the one hand, and the drive mechanism control 13, on the other hand the control unit 11 calculates the necessary parameters for the drive unit 12 which are needed to execute the relative movement between tool and workpiece along the calculated trajectory.

A method for calculating the expected removal capacity in the computing and control device 10 is explained in more detail below.

The trajectory is first divided, in the computing and control device 10, into a multiplicity of sections during which no linear feed of the workpiece is effected along the direction of feed. For each section, the position of swiveling of the tool and the depth of the tool in the workpiece can then be calculated at various points. In principle, therefore, the trajectory can be represented by a multiplicity of numerical triplets, where the first numerical value of each triplet indicates the trajectory section, the second numerical value indicates the position of swiveling of the tool, and the third numerical value indicates the depth of the tool in the workpiece. If the workpiece additionally rotates about the feed axis, a further numerical value is used for the angle of rotation of the workpiece.

The calculation of the trajectory data does not have to be done completely for the whole trajectory before the start of grinding. It can also be done in sections: for example, during the grinding of one trajectory section, the data can be calculated in each case for the next trajectory section.

To explain the control of the relative movement between tool and workpiece, it is first of all assumed that the machining of a certain number of trajectory sections has already taken place. The computing and control unit 10 at this time contains at least the trajectory data from the last-machined trajectory section and the trajectory data for the next trajectory section to be machined. For each position of swiveling of the grinder rod, the computing and control unit 10 then compares the depth of the grinder rod in the workpiece at various points on the last-machined trajectory and on the trajectory to be machined next. This comparison determines the following two features:

- For each point of the trajectory, it is possible to 10 firstly calculate whether material is removed with the end face of the grinder rod. If this is the case, it is also possible to calculate approximately that portion of the end face of the grinder rod on which material removal takes place. A table was stored in advance in the computing and control unit 10, which table shows, for various portions of the end face on which removal takes place, the maximum permissible speed for the change of depth of the grinder rod in the workpiece. This maximum speed was earlier 20 determined empirically in the laboratory for the workpiece material in question.
- Likewise, the sectional comparison of the trajectory data permits calculation of that portion of the 25 circumferential surface on which material removal takes place. A further table was stored in advance in the computing and control unit 10, which table shows, for various values of the portion of the circumferential surface, the maximum permissible 30 speed for the swivel movement of the tool relative to the workpiece. Thus, by comparison with this table, the maximum permissible speed of swiveling can be determined for each point of the trajectory.

If the workpiece additionally rotates about the feed axis V, what has been stated above also applies analogously for the maximum speed of rotation of the workpiece about this axis.

The computing and control device 10 now sends signals to the control unit 11, which signals are able to trigger the drive mechanism for swiveling the tool and changing the depth of the tool. If the drive mechanism includes stepping motors, for example, the computing and control device 10 supplies the control device 11 with information concerning the number of adjustment steps of the stepping motor to be made at each trajectory point and the time sequence of these adjustment steps. The time sequence of the adjustment steps establishes in particular the speed of the relative movement. It is chosen such that this speed lies near to, but below, the calculated maximum permissible speed.

Using these signals, the control device 11 directly controls the drive mechanisms for the swiveling movement and change of depth of the tool and, at the end of each trajectory section, the drive mechanism for advancing the workpiece. In so doing, it receives from control device 13 information on the instantaneous loading of the grinder rod. Under optimum conditions, that is to say exact adjustment of the tools, a new and thus powerful grinder rod, optimum cooling etc., the determined instantaneous loading will substantially agree with the calculated loading. In this case, the control device does not need to intervene. However, if the grinder rod is worn and thus less efficient than expected, or if there are other non-optimum operating conditions, the actual loading of the grinder rod will be higher than the calculated loading. In this case, the control device 11 intervenes by lowering the relative speed between tool and workpiece.

The combination of an advance calculation of the expected loading and a determination of the actual instantaneous loading for the purpose of controlling the relative movement between tool and workpiece affords a number of advantages, of which some are mentioned here:

- The speed of movement of the grinder rod can be increased considerably at positions at which there is only slight removal of material. This results in a shorter overall machining time for preparing a workpiece. This is of particular importance if the workpiece is to be used to prepare a dental 10 prosthetic fitting which is to be fitted directly in the patient's mouth at the dental practice.
- The forces between workpiece and grinder rod are considerably reduced, particularly at those positions where a lot of material has to be removed, as a result of the speed of movement being reduced at these positions. This is of particular importance when filigree formations with low material thickness are to be made. In the event of excessive force between grinder rod and workpiece, such formations can easily break. Moreover, breaking of the grinder rod is prevented.
- Adequate cooling of the grinder rod is ensured in all conceivable operating situations. Upon detection of high loading of the grinder rod, the control device 11 can under certain circumstances be set so that the grinder rod is even withdrawn completely from the tool. This permits rapid cooling of the loaded surfaces and washing-out of removed particles from depressions in the workpiece.
- The method can be used not only with a grinder rod, but equally well with other tools such as milling cutters or grinding and cutting wheels.
- Finally, the proposed method permits automatic detection of wearing of the grinder rod. Such detection can be effected by monitoring the frequency of intervention of the control 11 as a result of excessive loading of the grinder rod. If the intervention of the control over an extended period of time is too frequent, a suitable signal device may ask the user to change the grinder rod.

The control method according to the invention can often be implemented without changing the existing devices for the production of medical fittings. Such a device will in any event include a computing and control device which, after suitable programming, will be able to take over the function of the computing and control device 10 in FIG. 4. Likewise, many existing devices already have a control unit for the detection of overloading. Instead of a fixed maximum relative speed between workpiece and tool, this control unit is now given a variable maximum relative speed which depends on the particular point of the trajectory. Thus, it is possible to achieve very reliable control in a simple way and at low cost.

What is claimed is:

1. A method for the production of medical fittings, in particular dental fittings, in which a workpiece, from which the fitting is produced, has material removed from it by machining with a tool as a result of moving the tool in the workpiece, the tool and the workpiece executing a relative movement along a trajectory, and an actual loading of the tool as a result of moving the tool in the workpiece being used to control the speed of the relative movement, wherein an expected loading of the tool along the trajectory is calculated and is used to control speed of the relative movement.

2. The method as claimed in claim 1, wherein the tool is essentially cylindrically symmetrical and rotates about its axis of symmetry by means of a rotary drive mechanism.

3. The method as claimed in claim 2, wherein the measure for the actual loading of the tool is its frequency of rotation determined at an essentially constant power consumption of the rotary drive mechanism.

4. The method as claimed in claim 2, wherein the measure for the actual loading of the tool is the power consumption of the rotary drive mechanism determined at an essentially constant frequency of rotation.

5. The method as claimed in claim 2, wherein the relative movement between the tool and the workpiece includes all of the following types of movement:
   a) linear feed between the tool and the workpiece along a feed direction which is essentially perpendicular to the axis of symmetry of the tool;
   b) change of depth of the tool in the workpiece essentially along the axis of symmetry of the tool; and
   c) one-dimensional sideways movement between the tool and the workpiece along a predetermined path in a plane which is essentially perpendicular to the axis of symmetry of the tool.

6. The method as claimed in claim 5, wherein the one-dimensional sideways movement comprises a swiveling of the tool about an axis which is essentially parallel to the axis of symmetry of the tool.

7. The method as claimed in claim 5, wherein the relative movement between the tool and the workpiece moreover includes a pivoting of the workpiece about an axis which is essentially parallel to the feed direction.

8. The method as claimed in claim 5, wherein the tool is an essentially cylindrical grinder rod with a circumferential surface and an end surface.

9. The method as claimed in claim 8, wherein
   the linear feed takes place in steps which are small compared to the diameter of the grinder rod,
   the trajectory is divided into sections between which no linear feed takes place,
   and the expected loading for each section is calculated by comparison of the trajectory along this section and the trajectory along the previous section.

10. The method as claimed in claim 9, wherein, in order to determine the expected loading upon a one-dimensional sideways movement, the height of that portion of the circumferential surface of the grinder rod from which material is removed is calculated.

11. The method as claimed in claim 10, wherein the speed of the one-dimensional sideways movement is limited to a maximum speed which is determined by reference to a table in which, for a number of values of the height of that portion of the circumferential surface from which material is removed, the associated maximum speed is stored.

12. The method as claimed claim 9, wherein, in order to determine the expected loading upon a change of depth of the grinder rod in the workpiece, that portion of the end face approximately is determined from which material is removed.

13. The method as claimed in claim 12, wherein the speed of the change of depth of the tool in the workpiece is limited to a maximum speed which is determined by reference to a table in which, for several values of that portion of the end face from which material is removed, the associated maximum speed is stored.

* * * * *